(12) United States Patent
Marra et al.

(10) Patent No.: US 10,629,301 B2
(45) Date of Patent: Apr. 21, 2020

(54) SYSTEM AND METHOD FOR DETECTING THE PHYSICAL CONTACT EVENTS IN A HOSPITAL ENVIRONMENT, AND USE OF THE HUMAN BODY AS A MEANS FOR TRANSMITTING AN IDENTIFICATION SIGNAL IN A SYSTEM FOR DETECTING THE PHYSICAL CONTACT EVENTS IN A HOSPITAL ENVIRONMENT

(71) Applicants: Sociedade Beneficente Israelita Brasileira Hospital Albert Einstein, São Paulo (BR); I-HealthSys Produtos Médicos Ltda—ME, São Carlos (BR)

(72) Inventors: Alexandre Rodrigues Marra, São Paulo (BR); Marcelo Prado, São Carlos (BR); Renaldo Massini Junior, São Carlos (BR); Guilherme MacHado Gagliardi, São Carlos (BR); Tales Roberto De Souza Santini, Muzambinho (BR); Alvaro Costa Neto, São Carlos (BR)

(73) Assignees: Sociedade Beneficente Israelita Brasileira Hospital Albert Einstein, São Paulo (BR); I-HealthSys Produtos Médicos Ltda—ME, São Carlos (BR)

( * ) Notice: Subject to any disclaimer, the term of this patent is extended or adjusted under 35 U.S.C. 154(b) by 19 days.

(21) Appl. No.: 15/812,621

(22) Filed: Nov. 14, 2017

(65) Prior Publication Data
US 2019/0102520 A1    Apr. 4, 2019

(30) Foreign Application Priority Data
Sep. 29, 2017    (BR) .......................... 102017021006-5

(51) Int. Cl.
*G16H 40/63* (2018.01)
*G08B 25/10* (2006.01)
(Continued)

(52) U.S. Cl.
CPC .......... *G16H 40/63* (2018.01); *G06F 19/324* (2013.01); *G06F 19/3418* (2013.01);
(Continued)

(58) Field of Classification Search
USPC ................................................... 340/539.12
See application file for complete search history.

(56) References Cited

U.S. PATENT DOCUMENTS

| | | | | |
|---|---|---|---|---|
| 6,727,818 B1* | 4/2004 | Wildman | ............ | G06F 19/3418 340/573.1 |
| 2009/0267776 A1* | 10/2009 | Glenn | ..................... | G16H 40/20 340/573.1 |
| 2010/0073162 A1* | 3/2010 | Johnson | ............... | G08B 21/245 340/540 |
| 2010/0134296 A1* | 6/2010 | Hwang | ................ | A47K 5/1217 340/573.1 |

(Continued)

OTHER PUBLICATIONS

Thomas Guthrie Zimmerman, "Personal Area Networks (PAN) Near-Field Intra-Body Communication" Thesis for Master of Science in Media Arts and Sciences, Massachusetts Institute of Technology (MIT), Feb. 1980 (Year: 1980).*

*Primary Examiner* — Stephen R Burgdorf
(74) *Attorney, Agent, or Firm* — Patterson + Sheridan, LLP

(57) ABSTRACT

One describes a system for detecting the physical contact events in a hospital environment (4,4'), wherein the system comprises: at least one transmitting and receiving device (2,2') associated to a user (3,3') of the hospital environment (4,4'), a plurality of identifying devices (5) associated to a plurality of articles (6, 7, 8, 9, 10) arranged in the hospital environment (4,4'). The system for detecting the physical contact events in a hospital environment is configured to generate a cleaning signal (90) if the user (3,3') of the hospital environment (4,4') establishes physical contact with
(Continued)

at least one of the articles (6, 7, 8, 9, 10) arranged in the hospital environment (4,4'). Additionally, the cleaning signal (90) is generated if physical contact is established between different users (3,3') of the hospital environment (4,4'). One further approaches a method of detecting physical contact events in a hospital environment.

16 Claims, 9 Drawing Sheets

(51) Int. Cl.
    *G06F 19/00*         (2018.01)
    *G08B 21/24*         (2006.01)
    *G08B 21/02*         (2006.01)
(52) U.S. Cl.
    CPC ........... *G08B 21/245* (2013.01); *G08B 25/10* (2013.01); *G08B 21/02* (2013.01)

(56) References Cited

U.S. PATENT DOCUMENTS

| | | | |
|---|---|---|---|
| 2010/0328443 A1* | 12/2010 | Lynam | G06K 9/00771 348/77 |
| 2011/0254682 A1* | 10/2011 | Sigrist Christensen | G16H 40/20 340/539.12 |
| 2013/0113931 A1* | 5/2013 | Alper | H04N 7/18 348/143 |
| 2013/0122807 A1* | 5/2013 | Tenarvitz | H04B 5/0031 455/41.1 |
| 2015/0235550 A1* | 8/2015 | Pelland | G01S 5/02 340/573.1 |
| 2015/0287182 A1* | 10/2015 | Herger | G06T 7/0012 382/128 |
| 2016/0275779 A1* | 9/2016 | Hajdenberg | G08B 21/245 |
| 2019/0228640 A1* | 7/2019 | Freedman | G16H 40/20 |

* cited by examiner

SYSTEM AND METHOD FOR DETECTING THE PHYSICAL CONTACT EVENTS IN A HOSPITAL ENVIRONMENT, AND USE OF THE HUMAN BODY AS A MEANS FOR TRANSMITTING AN IDENTIFICATION SIGNAL IN A SYSTEM FOR DETECTING THE PHYSICAL CONTACT EVENTS IN A HOSPITAL ENVIRONMENT

The present invention relates to a system and a method for detecting physical contact events in a hospital environment. More specifically, the present invention relates to a system and a method capable of effectively detecting the occurrence of physical contact, not only between user and determined pieces of equipment, but also the occurrence of physical contact between two or more users. The invention further approaches the use of the human body as a means for transmitting an identification signal in a system for detecting physical contact events in a hospital environment.

DESCRIPTION OF THE PRIOR ART

Hand hygiene is a common practice required at hospitals for both health professionals and patients/companions and obviously aims at preventing or at least reducing the transmission of diseases and infections.

For this reason, at a hospital, one arranges a plurality of dispensers, most of the time comprising alcohol gel, so health professionals and passers-by (visitors) can correctly clean their hands. Besides said dispensers, hand hygiene can be done, obviously, at taps arranged inside hospitals.

The hand-cleaning habit is more usual within surgical centers, since at these places the interaction between patient and medical professionals is maximum, as well as the interaction between the health professional and pieces of equipment, utensils, objects, pieces of furniture that may be contaminated.

Further, with regard specifically to surgical procedures, a professional must brush his hands and arms before carrying out a surgical operation, and he must carry out a sequence of steps, so that such brushing can be properly carried out.

If any physical contact (touch) occurs between the doctor and determined pieces of equipment or else between two or more doctors during a surgical operation, it is necessary to clean one's hands. Similarly, if such contacts take place while brushing one's hands, one should restart the procedure.

A few proposals are known in the state of the art for hand hygiene at hospitals, which make use of radiofrequency to track movement and positioning of the medical professional. However, and as will be discussed later, such proposals lack in detecting effectively whether a physical contact between the professional and determined pieces of equipment has taken place indeed.

The knowledge disclosed in the prior art allows only to suggest or estimate that the physical contact may have taken place, mostly because such proposals make use of antennas arranged in determined environments (wards, rooms, corridors). However, the use of antennas only indicates that the medical professional is near a determined piece of equipment, but one cannot guarantee for sure whether a touch event has actually taken place.

As an example, one can mention the teachings of document PI 0704998, wherein a hand washing system, using radiofrequency, is proposed. Said system basically comprises patient stations (such as hospital beds), cleaning stations (hand washing points) and patient-identifying labels. One further cites that each patient station and cleaning station will have a coupled identifier.

Starting from the use of the identifiers at the patient stations and cleaning stations, as well as from the patient-identifying labels, document PI 0704998 states that interactions between patient and equipment can be tracked. Indeed, such a proposal allows one to estimate the position of a medical professional with respect to the pieces of equipment and hospital beds, by communication via radiofrequency between the plurality of labels and identifiers distributed inside the hospital.

However, the estimate of the position within the hospital environment alone is not sufficient to determine whether there has been physical contact between professionals and determined pieces of equipment. For example, the teachings of PI 0704998 enable one to estimate that the doctor is close to a determined piece of equipment, but such an estimate of proximity is not sufficient to guarantee that a physical contact (touch) between the medical professional and said equipment has really taken place.

In a similar way, document US 2014/0266692 discloses a method and system that aim at potentiating hand-cleaning practices. In such a proposal, one can detect whether a professional is near a determined piece of equipment or table, but the professional may be beside the equipment, not touching it. So, such systems fail to detect effectively the occurrence of touch between the doctor and the equipment.

Some systems disclosed in the prior art can even determine the occurrence of touches between professionals and pieces of equipment, but these are totally dependent upon the place (position) in which a determined identifying device is arranged on the health professional or even on determined pieces of equipment.

For example, some systems will only operate if the doctor uses his identification tag associated to a determined specific portion of his body; otherwise, depending on its positioning, the communication between the identification tag and the system antenna may not take place. Similarly, systems known in the state of art fail to detect the occurrence of physical contact when the health professional touches a determined piece of equipment with the back portion of his body, or even when the touch is made with an arm that does not make use of an identification bracelet.

It is known that, at certain surgical center, the health professional will be located close to determined pieces of equipment, but without effectively touching them. Thus, it is understood that the prior-art teachings are valid to track the doctor's positioning, but they do not provide an efficient solution to evaluate truly whether a physical touch has actually taken place, which is the focus of the present invention.

Further, some systems disclosed in the prior art that propose to detect the occurrence of touches between professionals and pieces of equipment require the user to use a determined component directly in contact with his skin, so that the occurrence of touches can be detected.

In some systems, the detection of touches takes place through the displacement of an electric driving current between the device associated to the doctor's skin and the device associated to the element at which one wishes to detect the touch, that is, with physical contact between the skin and the devices. This detection has some disadvantages, as will be set forth hereinafter.

Since this detection form needs that a determined device should be directly associated to the doctor's skin (such as a bracelet, a watch), it is based on transmission, by the skin, of an electric current directly coupled to the device. In this regard, it is known that, in many cases, the path travelled by an electric current may not be properly controlled. So, such a conduction form may eventually cause electric shocks applied to the doctor's body.

Thus, the detection of touches via electric current with direct coupling may jeopardize the safety of the user due to the occurrence of electric shocks. Moreover, said current may interfere with a pacemaker may be used by the user, and may further cause fibrillation or cardiac arrhythmia.

Moreover, the transmission via electric current with direct coupling through the skin may also interfere with the operation of determined pieces of equipment arranged in a medical environment. For example, said current may affect the operation of the electrocardiogram equipment, thus jeopardizing the safety of the patient and affecting the correct use of the equipment. Additionally, said form of detection via transmission of electric current may be made unfeasible if the user makes use of some type of clothes that acts as electric insulation, for example, gloves. In this regard, it is known that wearing gloves is usual in medical environments (such as certain surgical centers).

Thus, there are a number of disadvantages related to the detection of touches through transmission of an electric current by the skin of a determined user with direct electric coupling to the transmitting and receiving devices.

The present invention provides a system and a method that truly indicate to the health professional or to the hospital management that a physical contact has taken place between the health professional and any piece of equipment arranged inside the hospital.

The teachings of the present invention are specifically beneficial for monitoring and detecting the physical-contact events within surgical centers or still during the practice of brushing ones hands compulsorily by professionals before carrying out surgery operations. For instance, the present invention enables one to detect the occurrence of touch between the arm of a health professional and the aluminum sink usually arranged in rooms adjacent the operating room.

As an additional advantage, one considers that the present invention further enables one to detect the occurrence of physical contact between two or more health professionals. For instance, with the teachings of the present invention it becomes possible to evaluate whether there has been contact between the arms of two surgeons during the hand-brushing process, a situation in which the hand-brushing process should be repeated.

For the purpose of detecting the occurrence of touches, the present invention, unlike the concepts known from the prior art, is based on capacitive coupling between the transmitting and receiving devices associated to the health professional and the transmitting and receiving devices associated to the objects on which touches are to be detected, dispensing with the physical contact between them. Thus, in the present invention the problems relating to the transmission of an electric current through the user's skin with direct coupling to the devices are non-existent.

OBJECTIVES OF THE INVENTION

The present invention has the objective of providing a system for detecting physical contact events in a hospital environment, which is capable of detecting the occurrence of touches between health professionals and any piece of equipment arranged in the hospital environment.

It is an additional objective of the present invention to provide a system for detecting the physical contact events in a hospital environment, which is capable of detecting the occurrence of touches between two or more health professionals.

The present invention has also the objective of providing a system for detecting physical contact events in a hospital environment, capable of being used at surgical centers (operating rooms).

A further objective of the present invention is to provide a system for detecting physical contact events in a hospital environment, capable of being used for detecting the occurrence of touches during the hand brushing procedure carried out by health professionals before a surgical operation.

It is also an objective of the present invention to provide a system for detecting physical contact events in a hospital environment, which uses the human body itself as a data transmission means.

The present invention has also the objective of providing a method for detecting the physical contact events in a hospital environment in harmony with the proposed system.

It is also an objective of the present invention to propose the use of the human body as means for transmitting an identification signal, said identification signal being associated to the occurrence of physical contact within the hospital environment.

BRIEF DESCRIPTION OF THE INVENTION

The objectives of the present invention are achieved through a system for detecting physical contact events in a hospital environment, the system comprising: at least one emitting and receiving device associated to a user in the hospital environment and at least one identifying device associated to said at least one article arranged in the hospital environment.

The system for detecting physical contact events in a hospital environment is configured so as to generate a hand-cleaning signal, if the user of the hospital environment establishes a physical contact with said at least one of the articles arranged in the hospital environment. The hand-cleaning signal is also generated if physical contact is established between different users of the hospital environment.

The present invention further relates to a method of detecting the physical contact events in a hospital environment, the hospital environment comprising: at least one emitting device associated to at least one user of the hospital environment and at least one identifying device associated to at least one article arranged in the hospital environment, the method comprising at least one of the steps of: generating a hand-cleaning signal if the user of the hospital environment establishes physical contact with at least one of the articles arranged in the hospital environment and generating the hand-cleaning signal in case physical contact is established between different users of the hospital environment.

The objectives of the present invention are further achieved by using the human body as means for transmitting an identification signal capacitively coupled to it, the identification signal being associated to the occurrence of physical contact within the hospital environment.

BRIEF DESCRIPTION OF THE DRAWINGS

The present invention will now be described in greater detail with reference to an embodiment example represented in the drawings. The figures show:

FIG. 6 is a representation of a hand-brushing procedure carried out by a user before carrying out a surgical procedure, wherein

DESCRIPTION OF THE FIGURES

Figure 1:
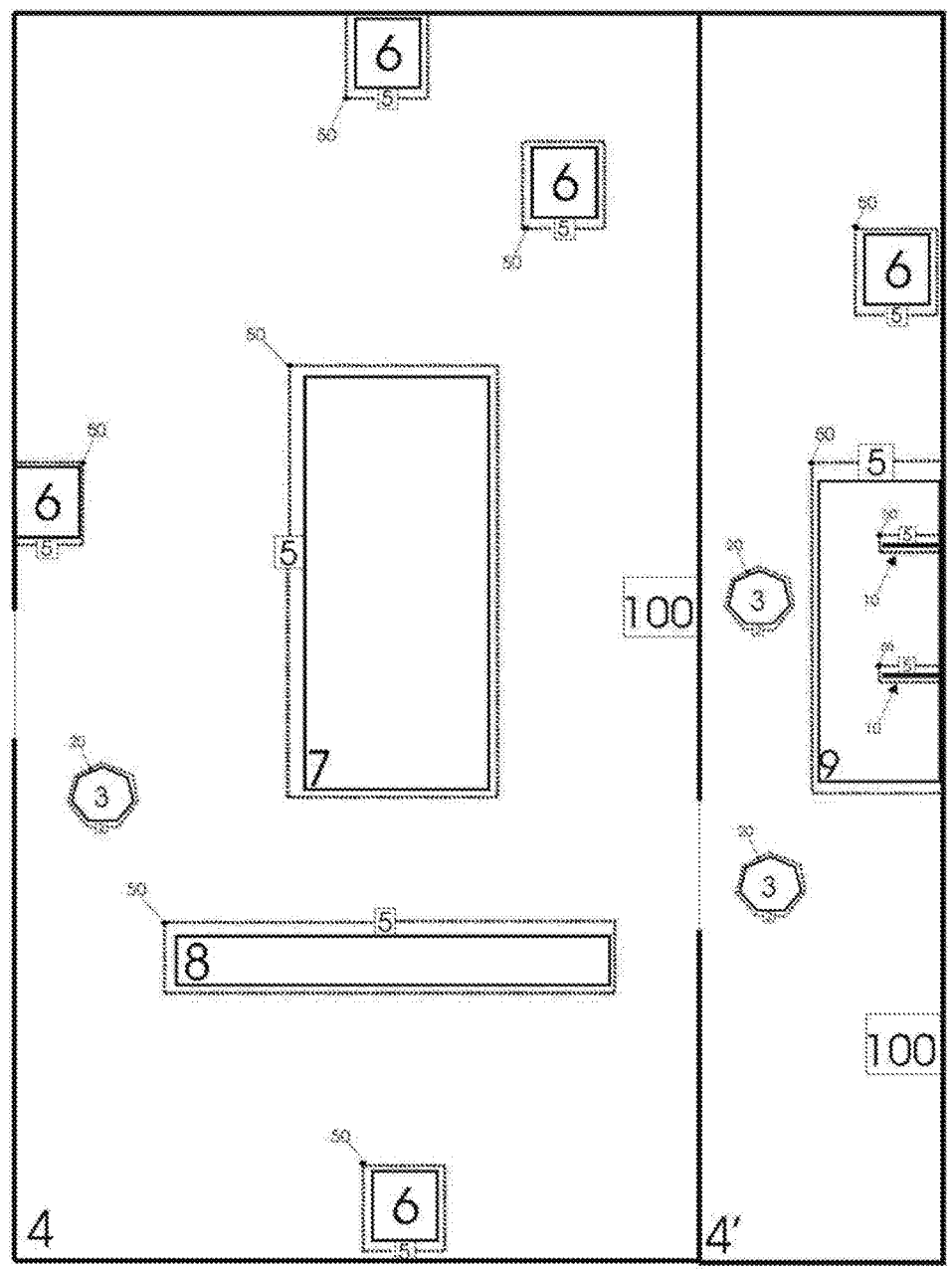
FIG. 1 represents a scheme of an embodiment of the system for detecting physical contact events in a hospital environment proposed in the present invention.

The present invention relates to a system for detecting physical contact events in a hospital environment. One points out that the reference to a hospital environment should be understood as being any health-treatment place, such as a hospital, including its surroundings, elevators, wards, rooms, meal serving areas, intensive treatment areas, surgical centers, brushing rooms, among others.

One may also interpret the hospital environment as a rest home, prompt care units, health centers, vaccination centers, emergency treatment centers, among others. Basically, any place related to health treatment should be understood as a hospital environment referred hereinafter.

As will be better discussed later, this embodiment of the system for detecting physical contact events in a hospital environment will make reference to a surgical center of a hospital or still to a brushing room usually arranged neighboring an operating room of a hospital. Obviously, such references should not be considered limitations of the present invention.

By "physical contact" one should understand the occurrence of a touch between a user of the hospital environment and a determined article arranged inside the hospital. The user of the hospital environment should be understood as a health professional. Alternatively, the teachings of the present invention may be perfectly absorbed by any person who is inside the hospital, such as visitors, accompanying individuals, male nurses, attendants, surgical nurses, among others.

By "articles arranged in the hospital environment" one should understand any piece of equipment or instrument on which one wishes to detect the occurrence of a touch. In this embodiment, as will be better discussed hereinafter, said articles should be understood as pieces of equipment arranged inside a surgical center and still in the brushing room thereof.

It is pointed out that the system proposed in the present invention allows not only the detection of the occurrence of physical contact between the health professional and the pieces of equipment (articles) arranged in the hospital environment, as well as the occurrence of physical contact between two or more health professionals.

For this purpose, the system and method proposed in the present invention use the human body itself (and the device on which one wishes to verify the occurrence of touch) as means of transmitting the signal relating to the occurrence of touch (identification signal). More specifically, the present invention is based on the communication by means of the human body, or the so-called intra-body communication.

Intrabody Communication

Said intra-body communication employs the human body as means of propagating electric signals for transmitting data. The working principle lies in the capacitive coupling of near field electromagnetic radiations in the human body, so that the transmitted signal is confined in a nearby region.

The transmitting and receiving devices are capacitively coupled to the body by means of conducting elements installed in contact with the body or in its close proximity. These conducting elements, called electrodes, are usually metallic, but they may also be made from other conducting materials. In this context, the conductive tissues of the human body also function as an electrode, providing transmission means between the electrodes of the transmitting and receiving devices, enabling them to exchange data through electric signals.

In order for the intrabody communication to be possible, it is necessary that the transmitter and the receiver share a potential reference, called common ground-potential. The common ground potential is provided by air, ground and by the conducting and/or dielectric objects that compose the environment near the devices, which are capacitively coupled to this environment by means of a second electrode, installed on each of them.

In a simplified manner, the interactions between the pairs of adjacent electrodes of the system may be approximated by parallel-board capacitors. In this model, the two conductors (for example, conductors associated to two health professionals and a piece of equipment), separated by a region of length d filled with dielectric material (for example, air, clothes and non-conductive human tissues), exhibit a capacitance C that measures amount of electric charge Q which the capacitor stores on boards in the presence of a potential difference (voltage) V among them, namely $C=Q/V$.

Thus, the greater the value C the more strongly the two conductors will be coupled capacitively, said value being inversely proportional to d (distance between the conductors), directly proportional to the surface area of the electrodes and affected by the type of dielectric existing between them.

In the situation in which the voltage V is applied between the capacitor boards by a transmitting device, an electric field of intensity $E=V/d$ develops between them. By applying a time-variable voltage V, the boards are charged and discharged according to this variation, and one will have an electric field that also varies in time according to V. This characterizes the near field radiation, propagated through the capacitive couplings and the human body itself. The variation of the electric field may be detected by adequately constructed receiving devices. Then the way for communication between the transmitting and receiving devices is established.

A modulation scheme may be imposed on the time-variable voltage V, so that massages will be encoded, which are propagated through the capacitive coupling between the conductors. The system may then be used to send or receive information through data packages. The time-variable voltage V may be produced, for example, by a resonant circuit, set at a determined preferred transmission frequency.

Intrabody Communication Applied to the Present Invention

FIG. 1 illustrated a representation of the system for detecting physical contact events in a hospital environment, as proposed in the present invention, wherein said hospital environment should be preferably understood as a surgical center 4 and a brushing room 4' arranged adjacent to it.

One observes that the surgical center 4 comprises a plurality of articles arranged inside it, such as aseptic substance dispensers 6, a hospital bed 7 for accommodating a patient and a support bench 8.

Similarly, the brushing room comprises dispensers 6, a sink 9 and tap 10, so that the users 3 of the hospital environment can carry out the hand brushing procedure before carrying out surgical procedures.

Obviously, the plurality of articles 6, 7, 8, 9 and 10 arranged in the environments 4 and 4' should not be considered a limiting feature of the present invention.

In order for the occurrence of physical contact on one of the articles 6, 7, 8, 9 and 10 to be detected, these should receive a plurality of identifying devices 5 associated to them. Basically, one should associate the identifying device 5 to the portion of the article 6, 7, 8 and 9 on which one wishes to verify the occurrence of a touch, as will be better described later.

In this embodiment of the present invention, as already discussed before, each of the identifying devices 5 is configured as a conducting element, such as an electrode built from conducting boards. Such identifying devices 5 are preferably metallic, but may also be made from other materials such as metallized paper, textile materials and polymers and electricity conducting plastics (such as polyaniline, polypyrrole, polyacetylene and polythiophene).

In a configuration, such identifying devices 5 may be fixed, for instance, at the lower portion of tables, around the aseptic substance dispensers 6 and around beds 7 arranged in the hospital environment 4, 4'.

Thus, one observes in FIG. 1 that the identifying devices 5 are associated to each of the dispensers 6, bed 7, and support bench 8, thus enabling one to detect properly the occurrence of any physical contact, as will be described hereinafter.

In order for the occurrence of any touch on such articles to be duly detected, one proposes that the user 4 of the system, such as a health professional, should make use of an emitting and receiving device 2.

In this embodiment, the emitting and receiving device 2 is configured as a radiofrequency emitting/receiving device associated to the user 3, such as an identification tag, bracelet, or any equivalent means. Further, it is necessary that the emitting and receiving device 2 remains visible, so that it can be arranged in the dustcoat/pants pocket of the user 3. Thus, one understands that the place at which the emitting and receiving device 2 does not mean a limitation of the teachings proposed herein. Further, one understands that the emitting and receiving device 2 does not necessarily need to be in direct contact with the skin of the user 3. As already said, the device 2 may be arranged in the doctor's dustcoat pocket, a situation in which there is no direct contact with the skin.

More specifically, the emitting and receiving device 2 includes a near-field radiofrequency transmitter, a near-field radiofrequency receiver, a far-field radiofrequency transmitter (for example, Bluetooth, Zigbee or WiFi), a microcontroller and two electrodes. Just as the identifying devices 5, the electrodes of the transmitting and receiving device 2 are usually metallic, but they may also be made from other types of conducting material, such as metallized papers, textile materials and polymers and electricity conducting plastics (such as polyaniline, polyacetylene and polythiophene).

As will be discussed ahead, the near-field-transmitters and receivers of the device 2 are responsible for detecting the occurrence of physical contact between users and articles or between users themselves, so that the far-field radiofrequency transmitter is responsible for sending subsequently said physical contact event to a data collection central 100, as illustrated in FIG. 1.

Further, one points out that each emitting and receiving device 2 and each identifying device 5 should have a single identification number, so that one can identify the user and the article arranged in the hospital environment.

Further with reference to FIG. 1, one observes that the association of the emitting and receiving device 2 to the user 3 establishes an emission (and reception) zone 20 of the transmitter and receiver 2, said emission zone 20 corresponding to the limits of the body of the user 3 who makes use of the device 2.

In a similar way, the association of the identifying devices 5 to the articles 6, 7 and 8 establishes an identification zone 50 of each of said articles, said identification zone 50 corresponding to the limits of the article 6, 7, 8 wherein the identifying device 5 is associated.

Regarding FIG. 1, both the identification zone 50 and the emission zone 20 are represented by dashed lines and should be understood, respectively, as limits to each one of the articles 6, 7 and 8 of the body of the user 3. In other words, the identification zone 50 delimits a portion monitored by the identifying device 5 and the emission zone 20 delimits a portion monitored by the emitting and receiving device 2.

Figure 2:
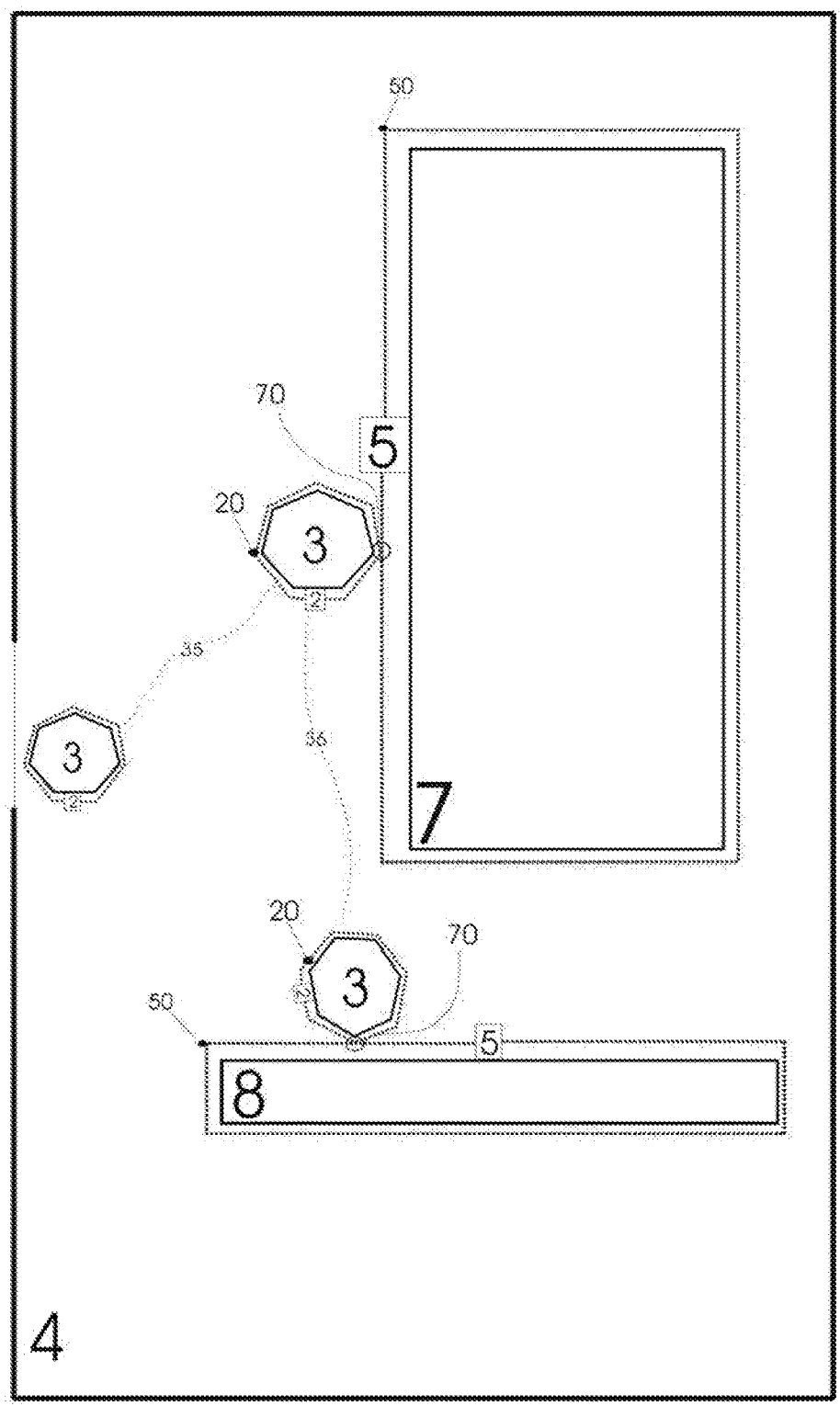
FIG. 2 represents a simplified scheme of the embodiment illustrated in FIG. 1.

With regard to the description referring to the occurrence of physical contact between the health professional 3 and one of the articles 7 and 8 of the surgical center 4, FIG. 2 illustrates a simplified representation of FIG. 1, in which only the bed 7 and the support bench 8 are illustrated together with the health professional 3.

One considers a scene in which the health professional 3 goes into the surgical center 4 and moves to the patient's bed 7, as indicated by the path 35 represented in FIG. 2.

Further with reference to FIG. 2, in the occurrence of physical contact (touch) between the body of the health professional 3 (that it, the portion delimited by the transmitting receiving device 2) and the limits of the bed 7 (that is, the portion delimited by the identifying device 5), a first contact intersection 70 will be identified.

Thus, by "first contact intersection 70" one understands the occurrence of intersection between the identifying zone 50 and the transmission zone 20, that it, there is intersection (indicated by the point 70) between the zones delimited by the identifying device 5 and by the transmitting and receiving device 2.

In a similar way, and considering now the path 36 travelled by a doctor 3 toward the support bench 8, the contact intersection 70 will be generated if, again, there is crossing between the identifying zone 50 and the transmitting zone 20.

In this way, one understands that the contact intersection 70 is established at the time of crossing (the occurrence of a common point) between the radiofrequency signals transmitted by the transmitting and receiving device 2 and by the identifying device 5, respectively.

In order for every and any physical contact between the health professional 3 and any of the articles 6, 7, 8,9 and 10 to be detected, the present invention proposes that the first contact intersection 70 be generated from an identification signal 60 transmitted by the identifying device 5, wherein said identification signal 60 being transmitted from the identifying device 5 to the transmitting and receiving device 2 associated to the health professional 3 and through a transmission means 80. In this way, one understands that the identification signal 60 is sent from the identifying device 5 to the transmitting and receiving device 2 of the surgical center.

Figure 3:
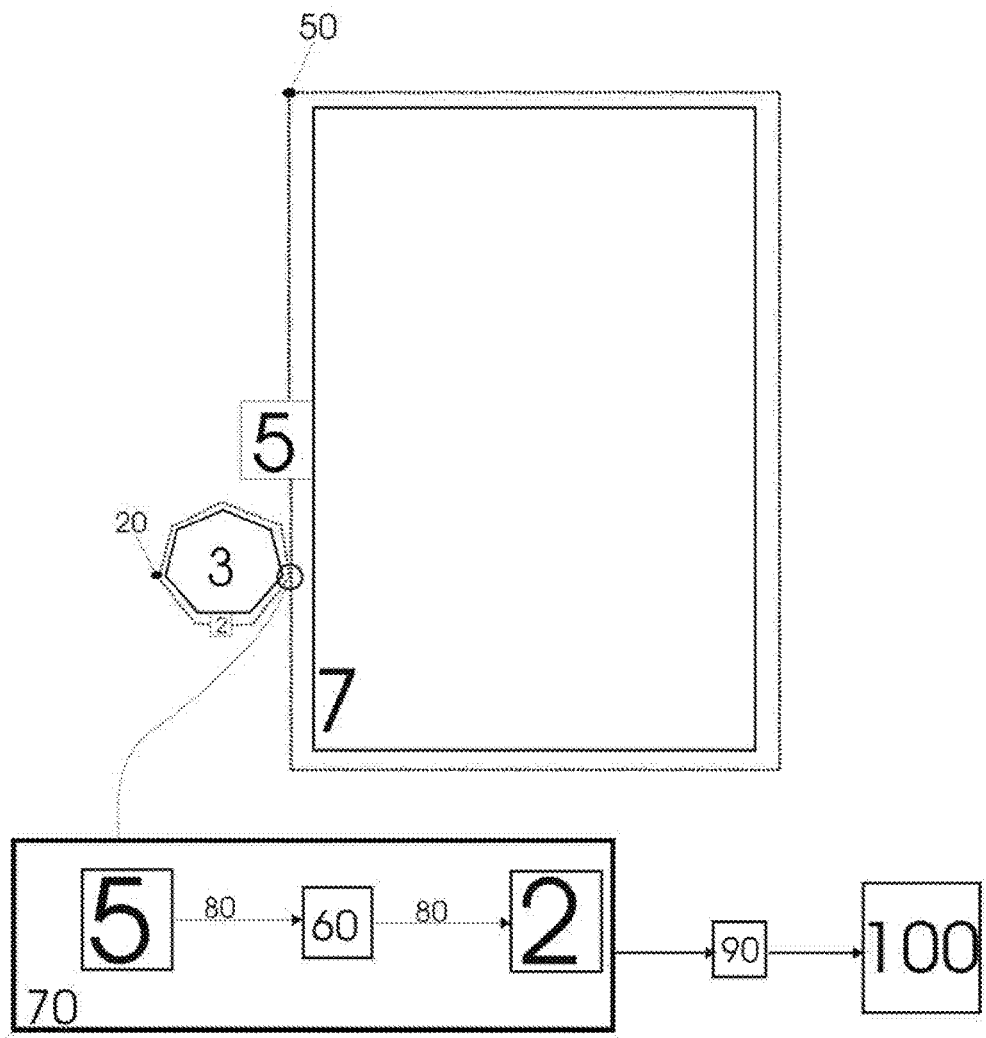
FIG. 3 represents a scheme illustrating the occurrence of contact between a user and an article arranged in the hospital environment.
Figure 7:
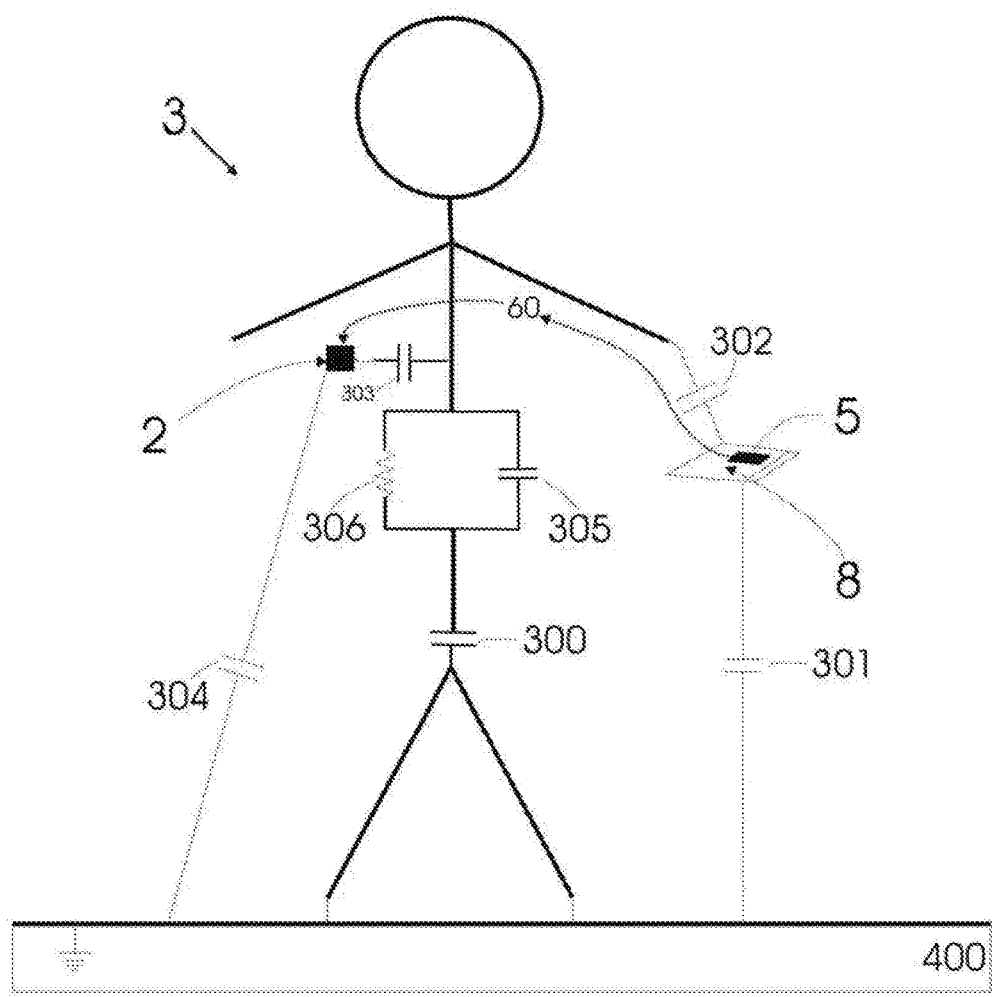
FIG. 7 is a representation, through a model of concentrated elements, of how the detection of occurrence of physical contact between a user and an article arranged in the hospital environment takes place, considering the concept of intrabody communication.

More specifically and with reference to FIGS. 2, 3 and 7, the teachings of the present invention propose that the identification signal 60 be transmitted directly from the identifying device 5 (associated to the article of the hospital environment) to the transmitting and receiving device 2 associated to the health professional.

Thus, one understands that the identification signal should "travel" the article of the hospital environment (in this case the bed 7 and the bench 8) and the health professional 3, thus reaching the transmitting and receiving device 2. In this way, one understands that the transmission means 80 should be understood as being the article itself of the hospital environment, as well as the body itself of the health professional.

In this way, it becomes unnecessary to use antennas for the system to operate correctly, since the present invention proposes the transmission of data through the human body itself, that is, through the body of the health professional and through the article arranged in the hospital environment.

Such feature ensured that the main objective of the present invention will be achieved, that is, the possibility of detecting touches, and that any touch between the doctor 3 and the articles arranged in the environment 4 will be duly detected, independently of whether this touch has taken place with one of the hands of the professional, with his back or any other body part.

In a more specific way, the identification signal 60 is configured as electromagnetic radiations with adequate frequency and transmitted from the identifying devices 5 to the transmitting and receiving device 2. In a preferred proposal, a frequency range from 50 kHz to 150 MHz would be acceptable.

With reference also to FIGS. 2 and 3, FIG. 7 illustrate a representation of how the detection of physical contact between the health professional 3 and an article arranged in the hospital environment, in this case the support bench 8, considering the concept of intrabody communication.

It is pointed out that the human body has intrinsic resistance 306 and capacitance 305, due to the resistive and capacitive properties of the human tissues. Assuming as potential reference the ground 400, one has the existence of a capacitance 302 between the human body and the electrodes of the identifying device 5, as well as a capacitance 303 between the human body and the electrodes of the transmitting and receiving device 2. It is further noted from FIG. 7 a capacitive coupling 304 between the transmitting and receiving device 2 and ground reference 400, as well as a capacitive coupling 301 between the identifying device 5 and ground reference 400.

With reference to FIG. 7, one further notes a capacitance 300 between the human body and the ground reference 400, so that the coupling between the human body and the ground potential 400 should be minimized, for instance, by using rubber shoes.

As already discussed before, the transmitting and receiving device 2 is capable of transmitting and receiving data through the human body, thereby detecting the identifying devices 5 associated to the articles within the hospital environment.

The communication between the transmitting and receiving device 2 and the identifying device 5 will take place when the distance between the body of the professional 3 (in the example of FIG. 7, his hand) is at such a determined minimum distance (detection distance) that the capacitive coupling developed, indicated by the capacitor 302, will be strong enough for the transmission path to be established. Said minimum distance may be configured for a centimeter distance, for example, or any minimum distance that indicates that a touch has occurred between the professional 3 and the article 8 (thus one understands that such a distance may be configured zero).

Thus, one understands that this detection distance may be set by the system, and it is possible to limit the detection to when the hand is in contact with the support bench 8 (detection distance equal to zero).

In this way, and also with reference to FIG. 2, one understands that the first contact intersection 70 is linked to the detection distance, that is, if the body (in this case, the hand) of the doctor 3 is at a distance equal to (or shorter than) the detection distance with respect to the support bench 8, the first contact intersection 70 will be generated and, as a result, the capacitance 302 will be sufficient to enable transmission of the first identification signal 60 from the identifying device 5 to the transmitting and receiving device 2, using, as transmission means, the support bench 8 and the body of the health professional, as shown in FIG. 7.

Thus, using the human body itself and the article (support bench 8) arranged in the hospital environment as data transmission means, the present invention enables detection of touches made by a health professional 3 to any article 6, 7, 8, 9, 10 arranged in the hospital environment.

An additional advantage of the system proposed in the present invention lies in the possibility of detecting not only the occurrence of contact between the user 3 with the articles 6, 7, 8, 9, 10, but also in the possibility of detecting the occurrence of touches between two or more health professionals 3, 3'.

It is known that during a surgical procedure the contamination chances are potentiated. So, if physical contact takes place between, for example, the arm of two surgeons during a procedure, it is necessary to clean one's hands before continuing the surgical operation.

Figure 4:
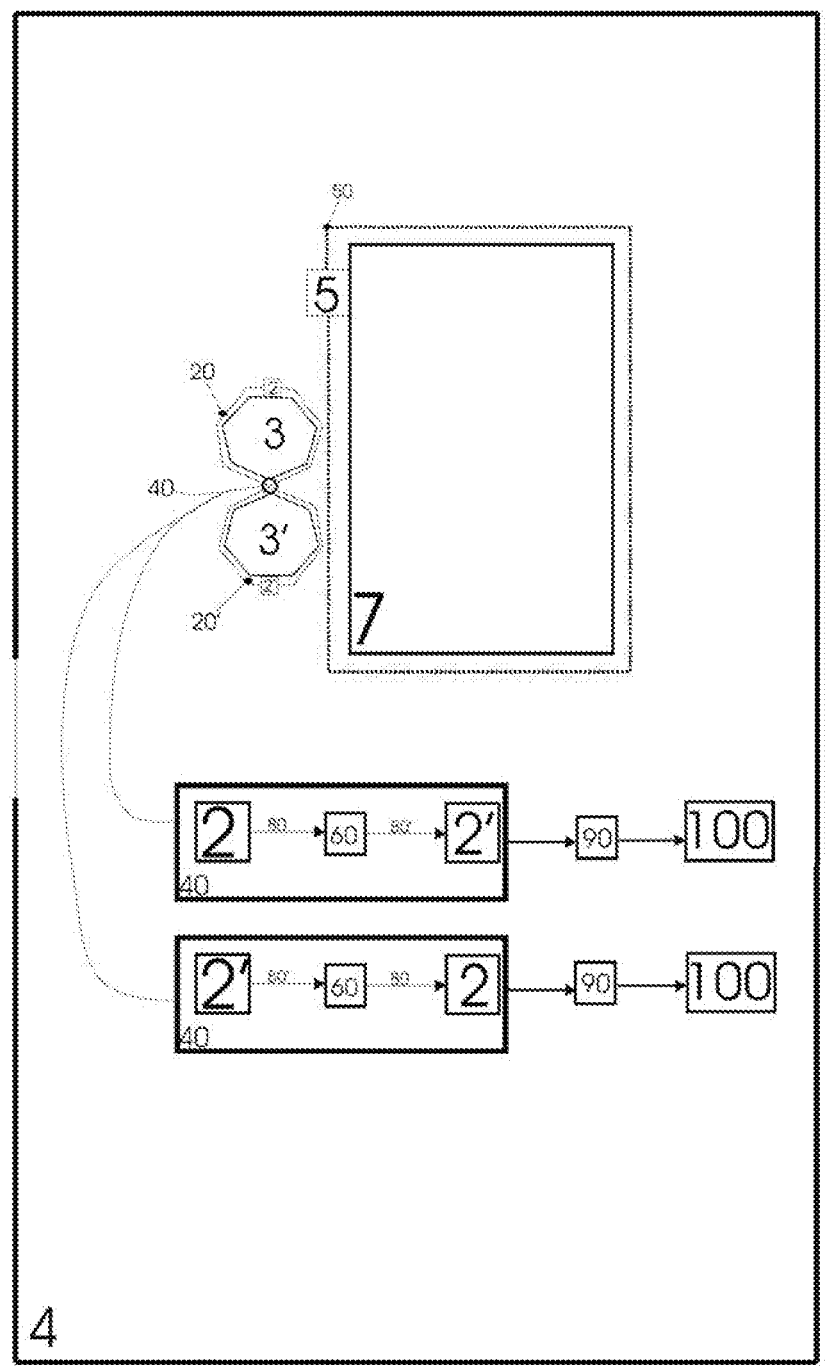
FIG. 4 represents a scheme illustrating the occurrence of contact between two users of a hospital environment.
Figure 8:
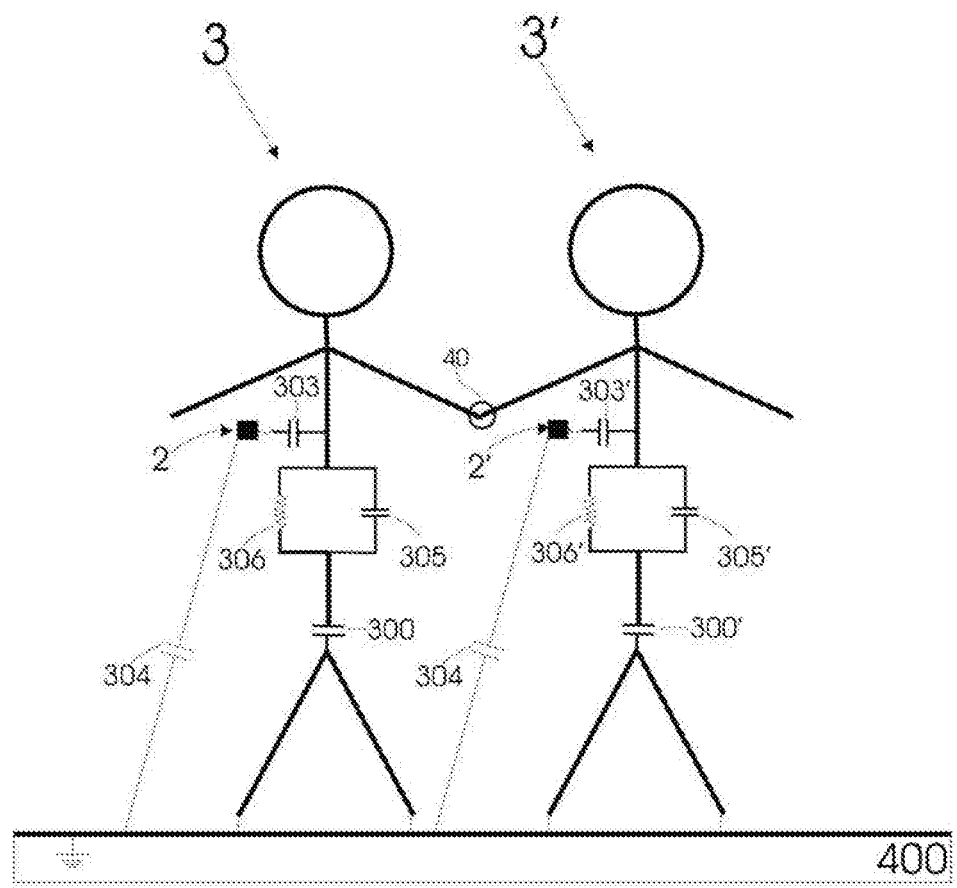
FIG. 8 is a representation, through a model of concentrated elements, of how the detection of occurrence of physical contact between two users takes place, considering the concept of intrabody communication.

In this way, and with reference to FIGS. 4 and 8, the occurrence of touch between different health professional, such as surgeons 3, 3', will be detected through the existence of a second contact intersection 40 between them. Thus, one understands that the second contact intersection 40 is generated when an intersection (crossing) occurs between two different emitting zones, such as zones 20 and 20' represented in FIG. 2 and respectively generated by the transmitting and receiving devices 2, 2'.

Once the occurrence of touch between the professionals 3, 3' has been detected, that is, once the second contact intersection 40 has been detected, one can say that communication is established between the identification signal 60 generated by each of the transmitting and receiving devices 2 and 2'.

In other words and further with reference to FIG. 4, one understands that the identification signal 60 generated by the transmitting and receiving device 2 of the doctor 3 is sent to the transmitting and receiving device 2' of the surgeon 3', and vice-versa. That is, in this way, the emitting and receiving device 2 will send an identifying signal 60 to the emitting and receiving device 2' and, in a similar way, the emitting and receiving device 2' will send the identifying signal 60 to the emitting and receiving device 2.

In a similar way, the description made before at the time of occurrence of touches between the professional 3 and the article arranged in the hospital environment, such data transmission uses, as transmission means 80 and 80', the body itself of the doctors 3 and 3', respectively.

FIG. 8 illustrated a representation of how the detection of occurrence of physical contact between two health professionals 3 and 3' takes place, considering the concept of intrabody communication.

In this case, each professional 3 and 3' has a respective transmitting and receiving device 2, 2' with an identifying number of his own. At the time of physical contact between the two professionals (that is, when the distance between the professionals is equal to or shorter than the detection distance set previously), such devices 2 and 2' will detect said event and, as a result, the second contact intersection 40 and the identification signal 60 will be generated.

Figure 9:
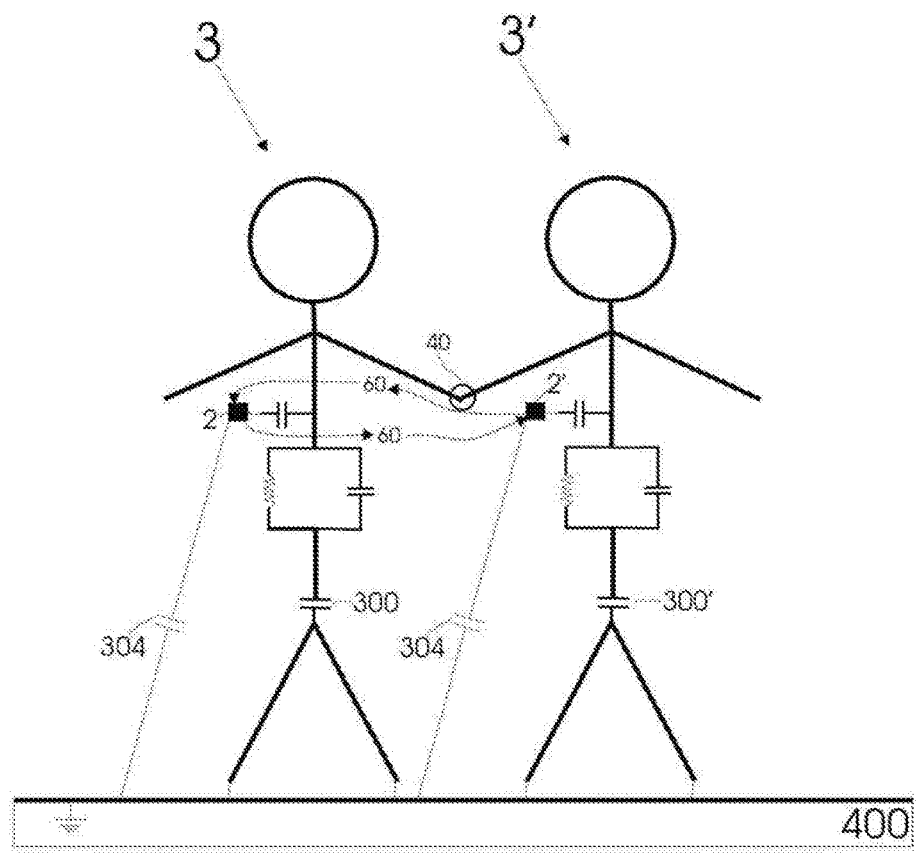
FIG. 9 is a representation, through a model of concentrated elements, of the transmission of the identifying signal between different users of the hospital environment.

Thus, the transmission of the identification signal 60 between the devices 2 and 2' will take place, using the human body as transmission means and as represented in FIGS. 9.

Figure 5A:
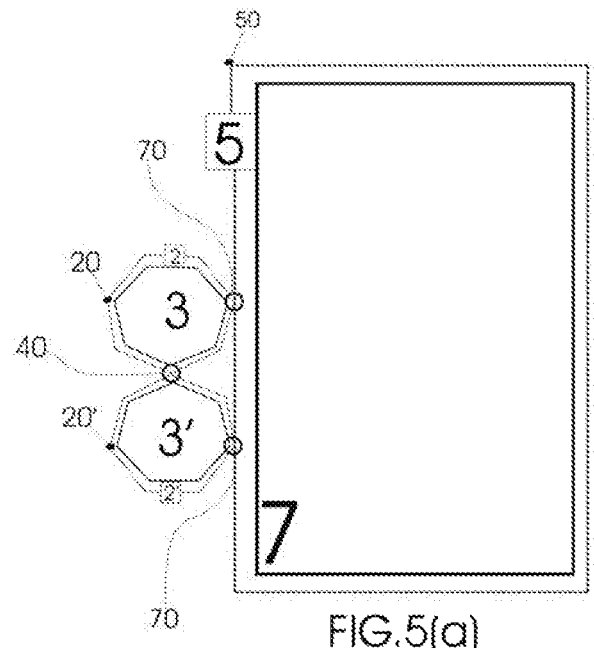
FIG. 5 represents a scheme illustrating the occurrence of contact between users with articles of a hospital environment wherein FIG. 5(a) illustrate the occurrence of contact between two users wherein both establish contact with the article, and FIG. 5(b) illustrated the occurrence of contact between two users wherein only one of them establishes contact with the article of the hospital environment.

It is pointed out that the system proposed in the present invention enables detection of the occurrence of contact not only between a doctor and an article (FIGS. 2, 3 and 7) and between two or more doctors (FIGS. 4, 8, and 9), but also the combination of such facts as the occurrence of contact between the doctors 3 and 3', while both still establish contact with the bed 7, as represented in FIG. 5(a). Thus, one understands that the present invention is capable of combining the generation of the first contact intersection 70 with the second contact intersection 40.

Figure 5B:
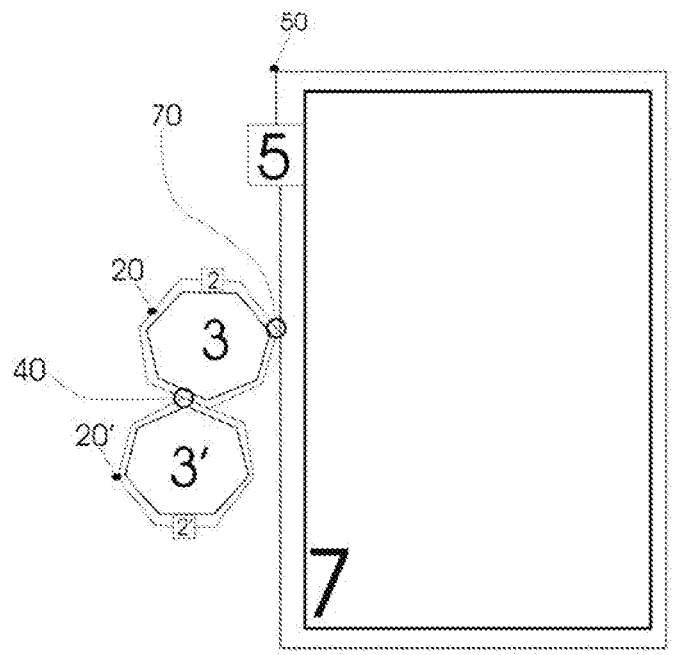

Obviously, the proposed system is also capable of detecting the occurrence of contact between two or more health professionals, such as surgeons 3, 3', represented in FIG. 5(b), in which only one of them establishes contact with the bed 7.

As already discussed before, the teachings of the present invention are still useful for detecting physical contact events within the brushing room 4' of a hospital environment, as represented in FIG. 1.

Thus, one may associate the identifying devices 5 to the dispensers 6 arranged in such a room, as well as to the existing sink 9 and tap 10 to carry out the brushing procedure.

Figure 6A:
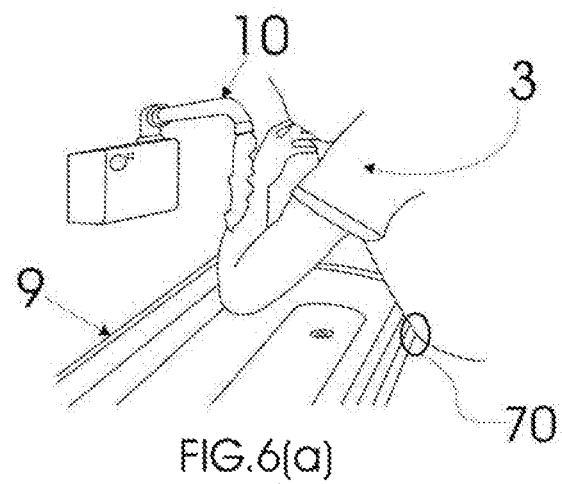
FIGS. 6(a), 6(b) and 6(c) illustrate the occurrence of touches of the user with an article of the hospital environment.
Figure 6B:
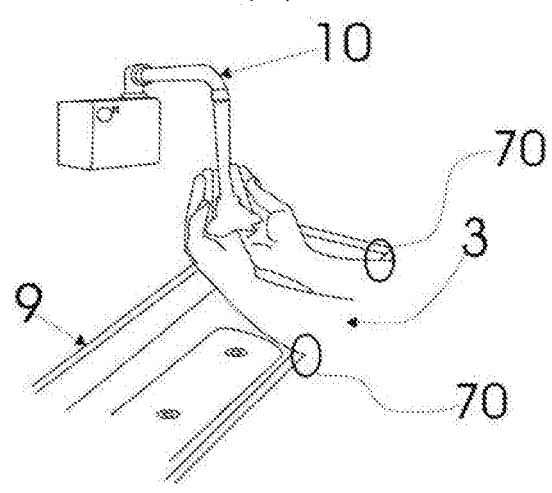
Figure 6C:
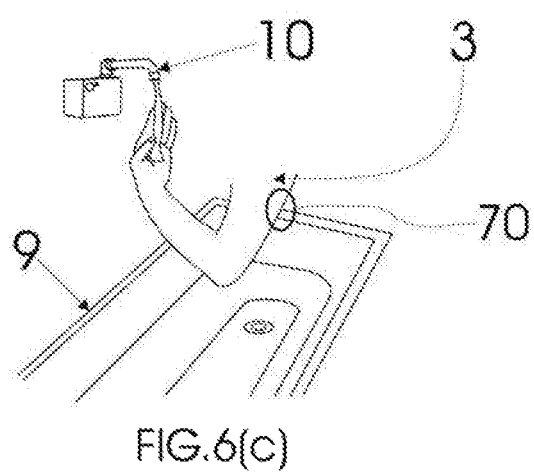

Specifically with regard to such a brushing procedure, it is known that it is generally carried out at an aluminum sink, such as the sink 9 represented in FIGS. 1 and 6.

Further, a specific technique is required for the surgical brushing, so that the brushing follows the hands almost as far as the elbows. All front, back and side faces should be brushed. When the surgeons 3 finish the brushing, they remove the soap with water flowing in the same direction, from the hand to the elbows.

These movements may cause the professionals 3 to touch the sides of the sink 9 or still the tap 10. If the brushing is carried out by more than one professional 3, there may be physical contact between them.

If there is any contact of the hands, wrist or forearm with the sink frame 9 or tap 10, or still if there is contact between two or more surgeons, the brushing process must be repeated.

With the system proposed in the present invention, and from the description made before, any contact between the body of the user 3 and the limits of the sink 9 or tap 10 will be duly detected from the generation of the first contact intersection 70. Similarly, and as described before, any contact between two or more health professional 3, 3' will be detected from the generation of the second contact intersection 40, which indicates the need to clean one's hand again.

With reference to FIGS. 3 and 4, the indication of the need to clean one's hands is made through a cleaning signal 90, said signal 90 being generated whenever there is physical contact between the health professional 3 and one of the articles 6, 7, 8, 9, 10, or if a physical contact takes place between two or more professionals 3, 3', as described before. Thus, one understands that the cleaning signal 90 is generated from the identification signal 60, as represented in FIGS. 3 and 4.

In an embodiment, the cleaning signal 90 is sent via radiofrequency by the transmitting and receiving device 2 (through its far-field transmitter) to a data collection central 100, said central also comprising a radiofrequency module. Said central 100 may be preferably arranged in each of the environments 4, 4' that use the system proposed in the present invention, as represented in FIG. 1. Alternatively, one may arrange a single central 100 in the management room of the hospital, in which information the occurrence of physical contact in various operating rooms would be reported.

It is further pointed out that the data received by the collection central 100 may be retransmitted to a management software of the system, thus enabling the generation of reports and the creation of databanks relating to the occurrence of physical contact.

The cleaning signal 90 comprises information (data) referring to the identification number of the transmitting and receiving device 2 (identification of the health professional 3), identification of the article 6, 7, 8, 9, 10 on which physical contact has taken place, date, time and duration of the physical contact event. Similar data is shown if the contact has taken place between two or more health professionals.

In an embodiment, the data collection central 100 may perceptively indicate the occurrence of touch directly in the operating room 4, or in the brushing room 4'. Such indication may occur through a red light indicating to the doctor 3 the need to clean his hands or repeat the brushing procedure.

If the surgical procedures or brushing procedures are made without the occurrence of touches, a green light may be permanently displaced at the data collection central 100.

Such perceptive indication of the cleaning signal 90 may further be given directly on the transmitting and receiving device 2 (identification tag) of the doctor 3, for instance, through light indication or vibrating alert.

The teachings of the present invention enable the data received by the central 100 to be compiled and a report on the occurrence of physical contact to be generated and sent to the management of the hospital environment.

Additionally, the transmitting and receiving device 2 may further determine how much time the professional 3 took to carry out the hand brushing procedure, called brushing time. In an embodiment, the brushing time might be obtained through the time passed between the first and the last touch of a user on the tap 10 or the sink 9, for instance, at a determined time interval. Thus, one can monitor if the brushing time of doctor 3 was enough to be considered acceptable by the hospital management, which could be, for example, 5 minutes.

Moreover, one can inform the health professional 3 present in the surgical center on the need to repeat the hand brushing, if a period of time also determined by the hospital management has passed. For example, in a preferred embodiment, a vibrating/light alert might be displayed on the transmitting and receiving device 2 of the health professional, if the latter remains within the surgical center for a period longer than four hours, a situation in which the four hour period might be determined by considering the last moment of physical contact of the health professional 3 on the tap 10 or sink 9.

In an alternative embodiment, said indication to the health professional 3 might occur through indications present at the surgical center itself, for example, through the data collection central 100. Further, obviously one should consider the four hour period as only a preferred description, not being a limitation of the present invention.

In harmony with the description made for the system for detecting physical contact events in a hospital environment, the present invention further relates to a method of detecting physical contact events in a hospital environment.

According to the description made before, the method of detecting physical contact events in a hospital environment comprises at least one of the following steps: generating a cleaning signal 90 if the user 3, 3' of the hospital environment 4, 4' establishes physical contact with at least one of the articles 6, 7, 8, 9, 10 arranged in the hospital environment 4, 4', and generating the cleaning signal 90 if physical contact is established between different users 3, 3' of the hospital environment 4, 4'.

As described before, the proposed method further comprises the step of generating an identification zone 50 associated to each of the articles 6, 7, 8, 9, 10 arranged in the hospital environment 4, 4', wherein the identification zone 50 comprises the limits of the article 6, 7, 8, 9, 10 to which the identifying device 5 is associated.

One further proposes the step of generating a transmission zone 20 corresponding to the limits of the body of the user 3, 3' who uses the transmitting and receiving device 2, 2'.

In harmony with the description made before, the proposed method further comprises at least one from the following steps: generating the cleaning signal 90 due to the existence of a first contact intersection 70 between the identification zone 50 and the emitting zone 20, and generating the cleaning signal 90 due to the existence of a second contact intersection zone 40 between at least two different emitting zones 20, 20'.

As described before, the method further comprises at least one of the following steps: transmitting an identification signal 60 from the identifying device 5 to the transmitting and receiving device 2, 2' through a transmission means 80, 80', when the first contact intersection 70 exists, and transmitting the identification signal 60 between emitting devices, 2, 2' of different users 3, 3' and through the transmission means 80, 80' when the second contact intersection 40 exists. In an embodiment, the transmission means 80, 80' is configured as the body itself of the user 3, 3' of the transmitting and receiving device 2, 2', or still as the body itself of the user, as well the article itself arranged in the hospital environment.

Additionally, and as described before, the identification signal 60 is configured as electromagnetic radiations with adequate frequency (from 50 kHz to 150 MHz).

In harmony with the description made before, one further approaches the use of the human body as transmission means 80, 80' for transmitting the identification signal 60 in a system for detecting physical contact events in a hospital environment 4, 4', wherein the hospital environment 4, 4' comprises at least one transmitting receiving device 2, 2' associated to at least one user 3, 3' of the hospital environment 4, 4' and at least one identifying device 5 associated to at least one article 6, 7, 8, 9 and 10 arranged in the hospital environment 4, 4'.

Thus, in harmony with the description made before, the use of the human body as transmission means 80, 80' for sending the identification signal 60 occurs due to at least one of: the generation of the identification signal 60 due to the occurrence of physical contact between the user 3, 3' and at least one of the articles 6, 7, 8, 9, 10 arranged in the hospital environment 4, 4' and the generation of the identification signal 60 due to the occurrence of physical contact between different users 3, 3' of the hospital environment 4, 4'.

Further, the identification signal 60 is transmitted from the identifying device 5 to the transmitting and receiving device 2, 2' upon occurrence of physical contact between the user 3, 3' and at least one of the articles 6, 7, 8, 9, 10 arranged in the hospital environment 4, 4', and the identification signal 60 is transmitted between the transmitting and receiving 2, 2' of different users 3, 3' of the hospital environment 4, 4' upon occurrence of physical contact between different users 3, 3' of the hospital environment.

Thus, one describes a system and method of detecting physical contact events in a hospital environment, capable of detecting the occurrence of touches between health professionals and also between professionals and determined articles arranged in the hospital environment. One also describes the use of the human body as transmission means for transmitting a signal relating to the occurrence of physical contact in hospital environments.

From the teachings of the present invention, it is not necessary to use antennas in the system, since the systems uses the body itself of the health professional 3 as transmission means to transmit the identification signal 60 generated by the identifying device 5, said identification signal 60 generating subsequently the cleaning signal 90, thus indicating the need to repeat the hand cleaning or brushing procedure.

Since one uses the human body itself as transmission means to transmit the identification signal 60, it is assured that any touch between the professional 3 and pieces of equipment 6, 7, 8, 9, 10 will be detected, regardless of which part of the body of the doctor 3 has made the touch or its position at the moment when the touch took place. Similarly, any touch between two or more doctors 3, 3' will duly detected.

With regard to the plurality of articles 6, 7, 8, 9, 10 discussed in the present invention, one should understand that the description of these as dispensers 6, bed 7, support bench 8, sink 9 and tap 10 should not be considered a feature limiting the present invention.

Obviously, the identifying device 5 may be associated to any element existing in a hospital environment, such as monitors, doors, door-nobs, pieces of furniture, television sets, windows, catheters, infusion pumps, probes, among others.

Thus, any element arranged in a hospital environment may be understood as an article capable of receiving the identifying device 5.

Thus, one proposes a system and method for detecting physical contact events in a hospital environment, as well as the use of the human body as transmission means to transmit a signal referring to the occurrence of physical contacts in a hospital environment. A preferred example of embodiment having been described, one should understand that the scope of the present invention embraces other possible variations, being limited only by the contents of the accompanying claims, which include the possible equivalents.

The invention claimed is:

1. A system for detecting physical contact events in a hospital environment during a hand brushing procedure, the hand brushing procedure being a sequence of steps that must be performed by a health professional to ensure hand hygiene before carrying out a surgical procedure, wherein the system comprises:
    at least one transmitting and receiving device associated with the health professional, the transmitting and receiving devices each establishing an emitting zone corresponding to the limits of a body of the health professional who uses the transmitting and receiving device,
    at least one identifying device associated with at least one article arranged in the hospital environment and used for carrying out the hand brushing procedure, each identifying device establishing an identification zone which corresponds to the limits of the articles to which the identifying devices are associated,
    wherein the system for detecting physical contact events in a hospital environment is configured to generate a cleaning signal if, during the hand brushing procedure, the health professional establishes a physical contact with at least one of the articles arranged in the hospital environment used for carrying out the hand brushing procedure,
    wherein the cleaning signal is further generated if a physical contact is established between different health professionals of the hospital environment during the hand brushing procedure,
    wherein the cleaning signal indicates to the health professional the need to initiate the hand brushing procedure again prior to the performance of the surgical procedure,
    wherein the cleaning signal is generated from an identification signal, the identification signal generated due to at least one of:
        existence of a first contact intersection between the identification zone and the emitting zone, and
        existence of a second contact intersection between at least two different emitting zones,
    wherein the identification signal is generated by at least one from the identifying device and the transmitting and receiving device.

2. The system according to claim 1, wherein the existence of the first contact intersection entails transmission of the identifying signal from the identifying device to the transmitting and receiving device through a transmission means, and
    the existence of the second contact intersection entails transmission of the identification signal between transmitting devices of different health professionals and through the transmission means.

3. The system according to claim 2, wherein the identification signal is configured as electromagnetic radiation with frequency between 50 kHz and 150 MHz.

4. The system according to claim 3, wherein the transmission means is configured as the body itself of the health professional that uses the transmitting and receiving device.

5. The system according to claim 4, wherein the transmitting and receiving device is configured to send the cleaning signal to a data collection central.

6. The system according to claim 5, wherein the identifying devices are associated with a plurality of articles arranged in at least one of a surgical center and a hand brushing room, wherein the plurality of articles is configured as:
    at least one aseptic substance dispenser, at least one hospital bed, at least one support bench, at least one sink and at least one tap.

7. The system according to claim 6, wherein the system is configured to detect a brushing time through the occurrence of a first physical contact and of a second physical contact between the health professional and one of the articles of the hospital environment used for carrying out the hand brushing procedure, said first and second physical contacts having occurred within a predetermined period of time.

8. A method of detecting physical contact events in a hospital environment during a hand brushing procedure, the hand brushing procedure being a sequence of steps that must be performed by a health professional to ensure hand hygiene before carrying out a surgical procedure, wherein the hospital environment comprises:
    at least one transmitting and receiving device associated with the health professional, the transmitting and receiving devices each establishing an emitting zone corresponding to the limits of a body of the health professional who uses the transmitting and receiving device,
    at least one identifying device associated with at least one article arranged in the hospital environment and used for carrying out the hand brushing procedure, each identifying device establishing an identification zone which corresponds to the limits of the articles to which the identifying devices are associated, wherein the method comprises at least one of the following steps:
        generating a cleaning signal if the health professional establishes a physical contact with at least one of the articles arranged in the hospital environment used for carrying out the hand brushing procedure, and
        generating the cleaning signal if a physical contact is established between different health professionals of the hospital environment during the hand brushing procedure,
    wherein the cleaning signal indicates to the health professional the need to initiate the hand brushing procedure again prior the performance of the surgical procedure,
    wherein the cleaning signal is generated from an identification signal, the identification signal generated due to at least one of:
        existence of a first contact intersection between the identification zone and the emitting zone, and
        existence of a second contact intersection between at least two different emitting zones,
    wherein the identification signal is generated by at least one from the identifying device and the transmitting and receiving device.

9. The method according to claim 8, the method further comprising at least one of the following steps:
- transmitting the identification signal from the identifying device to the transmitting and receiving device through a transmission means when the first contact intersection exists, and
- transmitting the identification signal between transmitting and receiving devices of different health professionals and through the transmission means when the second contact intersection exists.

10. The method according to claim 9, wherein the transmission means is configured as the body itself of the health professional that uses the transmitting and receiving device.

11. The method according to claim 10, wherein the identification signal is configured as electromagnetic radiation with frequencies between 50 kHz and 150 MHz.

12. The method according to claim 11, further comprising the step of:
- associating the identifying devices to a plurality of articles arranged in at least one of a surgical center and a hand brushing room, wherein the plurality of articles is configured as:
- at least one aseptic substance dispenser, at least one hospital bed, at least one support bench, at least one sink and at least one tap.

13. A system for detecting physical contact events in a hospital environment during a hand brushing procedure, the hand brushing procedure being a sequence of steps that must be performed by a health professional to ensure hand hygiene before carrying out a surgical procedure, wherein:
- the hospital environment is configured as at least one of a surgical center and a hand brushing room,
- wherein the system further comprises:
    - a plurality of identifying devices associated with at least one of the following articles: an aseptic substance dispenser, a hospital bed, a support bench, a sink and a tap arranged in the hospital environment, the identifying devices each establishing an identification zone which corresponds to a limit of the article to which the identifying devices are associated,
    - at least one transmitting and receiving device associated with the health professional, the transmitting and receiving devices each establishing an emitting zone corresponding to the limits of a body of the health professional who uses the transmitting and receiving device,
- wherein the system for detecting physical contact events in a hospital environment during a hand brushing procedure further comprises a cleaning signal, wherein the cleaning signal indicates to the health professional the need to initiate the hand brushing procedure again prior to the performance of the surgical procedure,
- wherein said cleaning signal being is generated due to at least one of:
    - an occurrence of a physical contact between the health professional of the hospital environment with at least one of the aseptic substance dispenser, the support bench, the sink and the tap during the hand brushing procedure, and
    - an occurrence of a physical contact between different health professionals of the hospital environment during the hand brushing procedure,
- wherein the cleaning signal is generated from an identification signal, the identification signal generated due to at least one of:
    - existence of a first contact intersection between the identification zone and the emitting zone, and
    - existence of a second contact intersection between at least two different emitting zones,
- wherein the identification signal is generated by at least one from the identifying device and the transmitting and receiving device.

14. Use of a human body as transmission means for transmission of an identification signal in a system for detecting physical contact events in a hospital environment during a hand brushing procedure, the hand brushing procedure being a sequence of steps that must be performed by a health professional to ensure hand hygiene before carrying out a surgical procedure, wherein the hospital environment comprises:
- at least one transmitting and receiving device associated with the health professional, the transmitting and receiving devices each establishing an emitting zone corresponding to a limit of a body of the health professional who uses the transmitting and receiving device,
- at least one identifying device associated with at least one article arranged in the hospital environment, and used for carrying out the hand brushing procedure, the identifying devices each establishing an identification zone which corresponds to a limit of the articles to which the identifying devices are associated, wherein the use of the human body as transmission means to transmit the identification signal occurs due to at least one of:
    - generation of the identification signal due to the occurrences of a physical contact between the health professional and at least one of the articles arranged in the hospital environment and used for carrying out the hand brushing procedure, wherein the occurrences of the physical contact between the health professional and at least one of the articles generates a first contact intersection between the identification zones and the emitting zones, and
    - generation of the identification signal due to the occurrence of a physical contact between different health professionals of the hospital environment, during the hand brushing procedure, wherein the occurrence of the physical contact between different health professionals generates a second contact intersection between at least two different emitting zones,
- wherein a cleaning signal is generated from the identification signal,
- wherein the cleaning signal indicates to the health professional the need to initiate the hand brushing procedure again prior the performance of the surgical procedure,
- wherein the identification signal is generated by at least one from the identifying devices and the transmitting and receiving devices.

15. The use of the human body as transmission means to transmit an identification signal in a system for detecting physical contact events in a hospital environment according to claim 14, wherein:
- the identification signal is transmitted from the identifying device to the transmitting and receiving device upon occurrence of the physical contact between the health professional and at least one of the articles arranged in the hospital environment, and
- the identification signal is transmitted between transmitting and receiving devices of different health professionals of the hospital environment upon occurrence of the physical contact between different health professionals of the hospital environment.

16. The use of the human body as transmission means to transmit an identification signal in a system for detecting physical contact events in a hospital environment according to claim 15, wherein the identification signal is configured as electromagnetic radiation with frequency between 50 kHz and 150 MHz.

* * * * *